United States Patent [19]
Pologe

[11] Patent Number: 5,297,548
[45] Date of Patent: Mar. 29, 1994

[54] ARTERIAL BLOOD MONITORING PROBE

[75] Inventor: Jonas A. Pologe, Boulder, Colo.

[73] Assignee: Ohmeda Inc., Murray Hill, N.J.

[21] Appl. No.: 45,962

[22] Filed: Apr. 12, 1993

Related U.S. Application Data

[63] Continuation-in-part of Ser. No. 832,551, Feb. 7, 1992.

[51] Int. Cl.⁵ .............................................. A61B 5/00
[52] U.S. Cl. ................................. 128/633; 128/665; 356/41
[58] Field of Search .......................... 128/633-634, 128/664-667; 356/39-41

[56] References Cited

U.S. PATENT DOCUMENTS

| | | | |
|---|---|---|---|
| 4,223,680 | 9/1980 | Jobsis | 128/633 |
| 4,824,242 | 4/1989 | Frick et al. | 128/666 X |
| 4,867,165 | 9/1989 | Noller et al. | 128/666 X |
| 5,078,136 | 1/1992 | Stone et al. | 128/666 X |
| 5,127,406 | 7/1992 | Yamaguchi | 128/633 |
| 5,137,023 | 8/1992 | Mendelson et al. | 128/633 |

FOREIGN PATENT DOCUMENTS

| | | |
|---|---|---|
| 0303502 | 2/1989 | European Pat. Off. |
| 9004353 | 5/1990 | PCT Int'l Appl. |
| 911136 | 8/1991 | PCT Int'l Appl. |

Primary Examiner—Angela D. Sykes
Attorney, Agent, or Firm—Roger M. Rathbun; Larry R. Cassett; James M. Graziano

[57] ABSTRACT

This arterial blood monitoring system takes advantage of the basic statistical property that arterial blood contains a plurality of dominant absorbers, whose measured light absorption spectra appear as a constant over a short interval of time. By measuring the transmitted light as it varies with arterial pulsation at selected wavelengths of light, over a common light path, the relative amount of these dominant absorbers in the arterial blood can noninvasively be determined. To ensure the common light path, a sandwich construction light detector is used.

10 Claims, 4 Drawing Sheets

ARTERIAL BLOOD MONITORING PROBE

CROSS-REFERENCE TO RELATED APPLICATIONS

This application is a continuation-in-part of U.S. patent application Ser. No. 07/832,551, titled "Improved Arterial Blood Monitoring System", filed Feb. 7, 1992, pending

FIELD OF THE INVENTION

This invention relates to non-invasive photoplethysmographic measurement of blood analytes and, in particular, to a probe for use in an arterial blood monitoring system to more accurately measure the change in intensity of the light transmitted through the arterial blood of a patient.

PROBLEM

It is a problem in the field medical monitoring equipment to accurately measure various parameters of arterial blood in a noninvasive manner. For example, the oxygen saturation ($S_a O_2$) of the hemoglobin in arterial blood is determined by the relative proportions of oxygenated hemoglobin and reduced hemoglobin in the arterial blood. A pulse oximeter system noninvasively determines the oxygen saturation of the hemoglobin by measuring the difference in the light absorption of these two forms of hemoglobin. Reduced hemoglobin absorbs more light in the red band (600–800 nm) than does oxyhemoglobin while oxyhemoglobin absorbs more light in the near infrared band (800–1000 nm) than does reduced hemoglobin.

The pulse oximeter includes a probe that is placed in contact with the skin, either on a flat surface in the case of reflectance probes or across some appendage in the case of a transmission probe. The probe contains two light emitting diodes, each of which emits a beam of light at a specific wavelength, one in the red band and one in the infrared band. The magnitude of red and infrared light transmitted through the intervening appendage contains a non-pulsatile component which is influenced by the absorbency of tissue, venous blood, capillary blood, non-pulsatile arterial blood, and the intensity of the light source. The pulsatile component of the received signals is an indication of the expansion of the arteriolar bed in the appendage with arterial blood. The effects of different tissue thicknesses and skin pigmentation in the appendage can be removed from the received signals by normalizing the change in intensity of the received signal by the absolute intensity of the received signal. Taking the ratio of the mathematically processed and normalized red and infrared signals results in a number which is theoretically a function of only the concentration of oxyhemoglobin and reduced hemoglobin in the arterial blood. This assumes that oxyhemoglobin and reduced hemoglobin are the only substantial absorbers in the arterial blood.

The amplitude of the pulsatile component is a very small percentage of the total signal amplitude and depends on the blood volume change per pulse and the oxygen saturation ($S_aO_2$) of the arterial blood. The received red and infrared signals have an exponential relationship to the path length of the arterial blood. The photoplethysmographic measurement of these analytes is predicated on the assumption that the light beams from the two light sources follow identical paths through the intervening appendage to the light detector. The greater the departure of the light beams from a common light path, the more significant the opportunity for the introduction of errors into the resultant measurements. This is especially true if multiple independent discrete light sources and multiple discrete light detectors are used in the probe, resulting in separate light transmission paths through the intervening appendage. The use of multiple light detectors, each sensitive to different wavelength regions, becomes a necessity if the wavelengths of light selected are far apart in wavelength, since there does not exist a single light detector device that can detect a wide bandwidth of light with significant speed, sensitivity and an acceptably flat response. Therefore, existing probe designs can introduce errors into the measurements by their inability to transmit a plurality of light beams substantially along a common light path through the arteriolar bed of the appendage being monitored.

SOLUTION

The above described problems are solved and a technical advance achieved in the field by the probe for an arterial blood monitoring system that creates a single light path through an appendage to noninvasively measure and calculate characteristics of arterial blood. This arterial blood monitoring system probe takes advantage of the basic statistical property that arterial blood contains a plurality of dominant absorbers, whose measured light absorption spectra appear as a constant over a short interval of time. The arterial blood characteristics to be measured are empirically related to the changes in the measured light transmission through the plurality of dominant absorbers as a function of the changes in arterial blood volume at the probe site. By measuring the transmitted light as it varies with arterial pulsation at a plurality of selected wavelengths of light, over a single common light path, the relative amount of these dominant absorbers in the arterial blood can noninvasively be determined.

By selecting one wavelength of light around 1270 nm, where water has a measurable extinction and second and third wavelengths at about 660 nm and 940 nm, a direct relationship between the transmitted intensities at these three wavelengths and the arterial hemoglobin concentration exists and can be calculated. The accurate detection of these three wavelengths of light is accomplished by the use of two different light detectors. To avoid the problem of different light paths through the intervening appendage, a sandwich or layered detector design is used in the probe. The light detector consists of a multiple layer element that contains a germanium photodiode placed under, and coincident with, a silicon photodiode. For the wavelengths of light shorter than approximately 1000 nm, the silicon photodiode receives the incident light and produces a signal indicative of the intensity of the received light. Above this wavelength, the silicon photodiode becomes transparent and the germanium photodiode picks up the incident light. Thus, the light from the three light sources is transmitted through the tissue along substantially identical light paths to be detected by the coincident light detectors at exactly the same "exit area", regardless of wavelength. By constraining the detected light to traverse one path through the tissue, regardless of wavelength, this apparatus avoids the inaccuracies caused by sampling different cross-sections of tissue, as with two or three discrete light detectors mounted side by side.

DETAILED DESCRIPTION

An arterial blood monitoring system takes advantage of the basic statistical property that arterial blood contains a plurality of dominant absorbers, whose measured light absorption spectra appear as a constant over a short interval of time. The arterial blood characteristics to be measured are empirically related to the changes in the measured light transmission through the plurality of dominant absorbers as a function of the changes in the arterial blood volume at the probe site. Therefore, by measuring the transmitted light as it varies with arterial pulsation, at selected wavelengths, the relative amount of these dominant absorbers in the arterial blood can noninvasively be determined. A single probe can be used to generate the plurality of wavelengths of light, therefore simplifying the arterial blood monitoring system.

Definition of Terms

Io = The intensity of the beam of light at a given wavelength incident on the tissue-under-test, where the wavelength is denoted by the subscript.

I = The instantaneous value of the intensity of the light received by the detector. The light is at a given wavelength, which wavelength is indicated by a subscript.

$\epsilon$ = The extinction coefficient of light by a given substance (indicated by a superscript) at a given wavelength (indicated by a subscript).

C = The concentration of a given substance (indicated by a superscript).

L = The pathlength of a given substance (indicated by a superscript).

tHb = Total hemoglobin measured in arterial blood. Usually expressed in terms of grams per deciliter.

O = Used as a superscript to represent oxyhemoglobin.

R = Used as a superscript to represent reduced hemoglobin.

W = Used as a superscript to represent water.

t = Used as a superscript to represent the combination of oxyhemoglobin and reduced hemoglobin.

System Architecture

Figure 1:
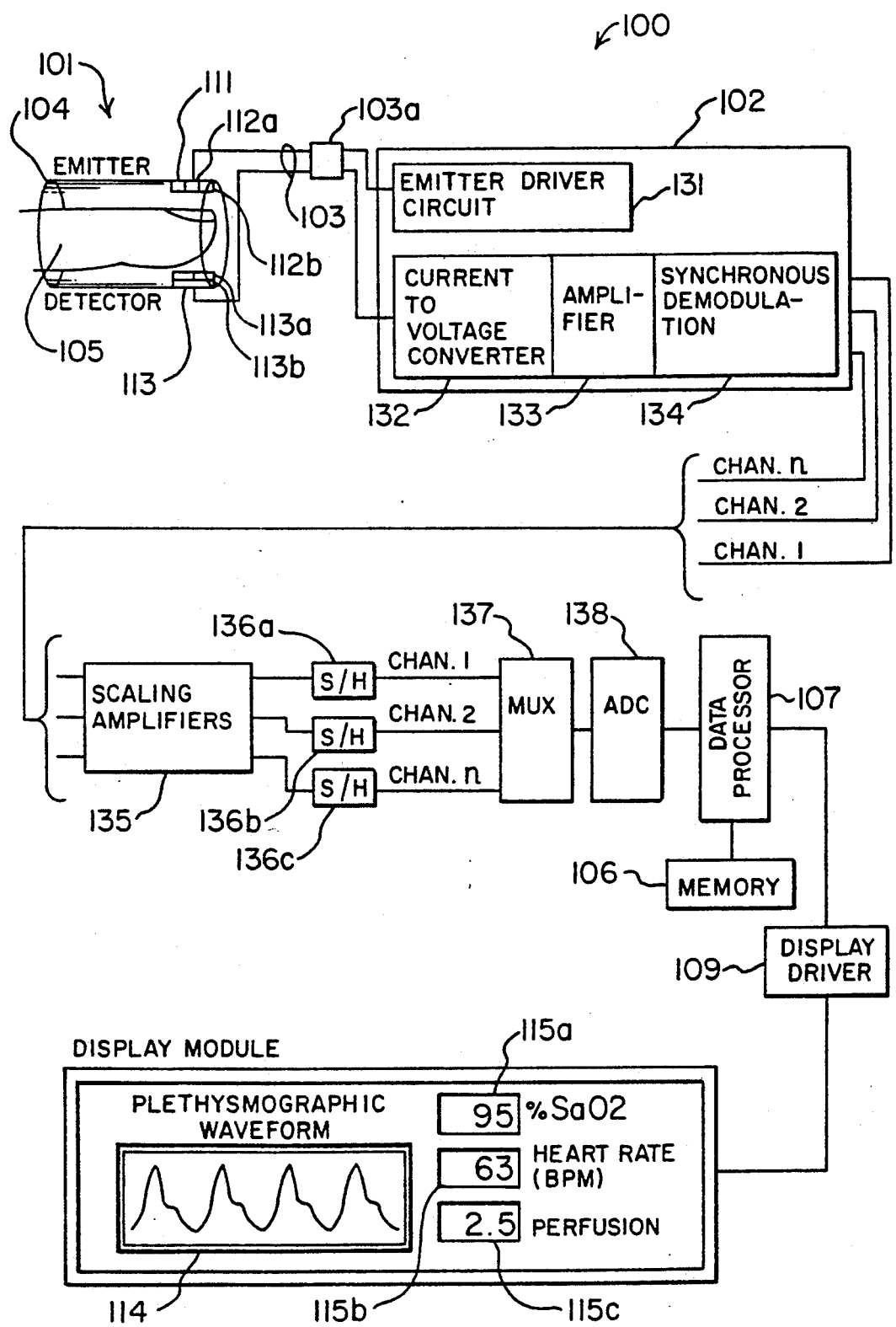
FIG. 1 illustrates in block diagram form the overall architecture of the arterial blood monitoring system and the probe of the present invention.

FIG. 1 illustrates in block diagram form the overall architecture of the arterial blood monitoring system 100 and the probe 101 of the present invention. The arterial blood monitoring system 100 consists of a probe 101 connected to probe interface circuit 102 by means of a set of electrical conductors 103 and connector 103a.

The probe 101 consists of an exterior housing 104 that applies the active elements of the probe 101 to the tissue under test, such as a finger 105, containing an arterial blood flow that is to be monitored. Included within housing 104 is a plurality (at least two) of light emitting devices 111, 112 and at least one corresponding light detector 113.

Emitter driver circuit 131 produces the analog drive signals to activate light emitting devices 111, 112 in probe 101. These analog drive signals are carried over cable 103 to probe 101. To measure the concentration of total hemoglobin (tHb), oxygen saturation ($S_aO_2$), or other blood analytes, in arterial blood, the concentration of several dominant absorbers contained in the arterial blood must be measured. In particular, for the measurement of total hemoglobin (tHb), concentration of the water and hemoglobin components of the arterial blood must be measured. The light emitting devices 111, 112 each produce an output light beam of predetermined wavelength which is directed at the finger 105 enclosed by housing 104. In this embodiment, light emitting device 111 is selected to produce a beam of light at approximately 810 nm, which wavelength is substantially isobestic to the oxygenated and deoxygenated components of the hemoglobin in the arterial blood (that is, the extinction coefficients of the oxygenated and deoxygenated hemoglobin are substantially identical). Light emitting device 112 is selected to produce a beam of light at approximately 1270 nm. The selection of these two wavelengths is such that water is transparent at the first wavelength of light (810 nm) but detected at the second (longer) wavelength of light (1270 nm). In addition, these wavelengths are such that the extinction coefficients of the two components (water and hemoglobin) differ at the first wavelength of light. Further, at both wavelengths the two species of hemoglobin are substantially isobestic in extinction but not transparent.

The light detector 113 monitors the level of light that is transmitted through or reflected from finger 105. The analog data signals produced by light detector 113 in response to the received beams of light are received from probe 101 over conductors 103 and filtered by analog hardware 132-134 in probe interface circuit 102. The input analog data from probe 101 may be decomposed into its non-pulsatile and pulsatile sub-elements in probe interface circuit 102 in order to provide accurate, high resolution, measurements of these components. The pulsatile component typically represents anywhere from 0.05% to 20% of the total input signal and the decomposition of the input signal into pulsatile and non-pulsatile components permits accurate analog to digital conversion of even the smallest of these pulsatile components.

In order to distinguish between the light beams produced by first 111 and second 112 light emitting devices, these light emitting devices 111, 112 are modulated in a manner to allow the output of the light detector 113 to be synchronously demodulated. Ambient light, being unmodulated, is easily eliminated by the demodulator process.

Signal Components

Figure 2:
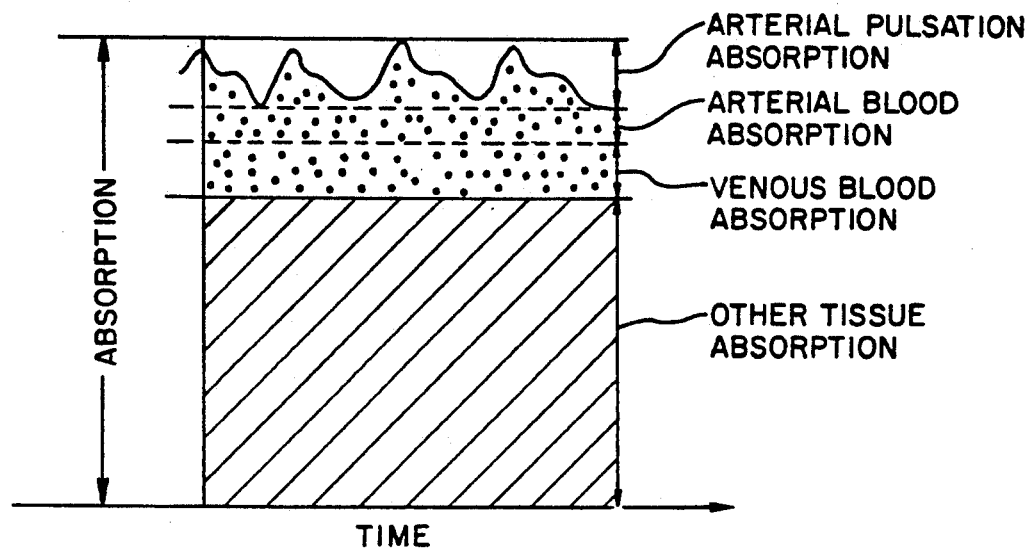
FIG. 2 illustrates in graphical form the various components of the input signal from the probe.

FIG. 2 illustrates in graphical form (not to scale) the various components of the total absorption produced by finger 105. The light detector output signal, high where absorption is low and visa versa, consists of a large magnitude non-pulsatile component and a small magnitude pulsatile component. The non-pulsatile component represents light remaining after absorption due to a combination of venous blood, cutaneous tissue, bone, and constant arterial blood while the small pulsatile component is caused by the light absorption due to pulsatile arterial blood flow that is to be measured. Following synchronous demodulation, the data signals produced by light detector 113 and transmitted to probe interface circuit 102 consist of a series of data points that are digitized and stored in memory 106. Since the first 111 and second 112 light emitting devices are sampled simultaneously and in rapid succession, these digitized data points consist of a plurality of sets of measurements, with one set corresponding to samples of the light beam intensity at a first wavelength, the other set corresponding to samples of the light beam intensity at a second wavelength, and, in some schemes, a third set corresponding to the intensity of the ambient light.

Ideally, in pulse oximeter systems red and infrared wavelengths of light are used and the ratio of the normalized derivative (or logarithm) of the red intensity to the normalized derivative (or logarithm) of the infrared intensity is a constant. This constant is indicative of the partial oxygenation ($S_aO_2$) of the hemoglobin in the arterial blood flow. It is obvious that this ratio changes as $S_aO_2$ changes but, for a short interval with rapid enough sampling rate, the ratio remains constant.

Probe Interface Circuit

The actual analog data received by the probe interface circuit 102 can include a fairly significant noise component which is caused by a number of sources including motion of finger 105, the introduction of ambient light into housing 104, and various sources of electrical noise. These noise components skew the values of either or both of the magnitudes measured in each set of data points destroying the correct relationship between the red and infrared signals. Existing pulse oximeter circuits make use of various filtering techniques to minimize the impact of noise on the $S_aO_2$ value measured by the system. This filtering circuitry and software/algorithms are analogous to that used in the arterial blood monitoring system 100 and are therefore not described in detail herein.

Probe interface circuit 102 includes emitter driver circuit 131 that is capable of driving light emitting devices 111, 112 such that the light beams produced traverse finger 105 and sufficient light intensity is incident on light detector 113 to produce data indicative of the light absorption of the dominant absorbers in arterial blood. The data produced by light detector 113 (voltage equivalent of the received light intensities) at each wavelength is kept distinct and can be processed independently. This can be done by any of the many schemes presently in use for pulse oximetry, such as time division multiplexing, or frequency division multiplexing.

The light received from finger 105 is converted to an equivalent current signal by the photodiodes of light detector 113, and then converted to a voltage signal by the current to voltage converter 132. The data is then amplified by amplifier 133, and demultiplexed via synchronous demodulation circuit 134. The demultiplexed data comprises analog voltage signals applied to leads CHAN 1, CHAN 2 ... CHAN n representative of the intensity of the received light at each of the wavelengths of light produced by light emitting devices 111, 112, respectively. The voltage signals on leads CHAN 1, CHAN 2 are then scaled (further amplification) by scaling amplifiers 135 such that they can be converted, with optimal resolution, to a digital equivalent. All channels output by scaling amplifiers 135 are then simultaneously sampled by the sample/hold circuitry 136a, 136b, ... 136n. The sampled data is passed a channel at a time via multiplexer 137 to the analog to digital converter 138. From there the data, now in digital form, is sent on to data processing circuit 107 where it is stored in memory 106 for processing. The digital data represents the substantially simultaneously sampled amplitudes of the received light intensities from each of the wavelengths used at a sampling frequency of typically 30 Hz or greater. These data values are referred to as $I_1, I_2, \ldots I_N$, where the subscript indicates the given wavelength. $I_n$ then indicates the received light intensity at any given wavelength.

Data Processing Circuit

Figure 4:
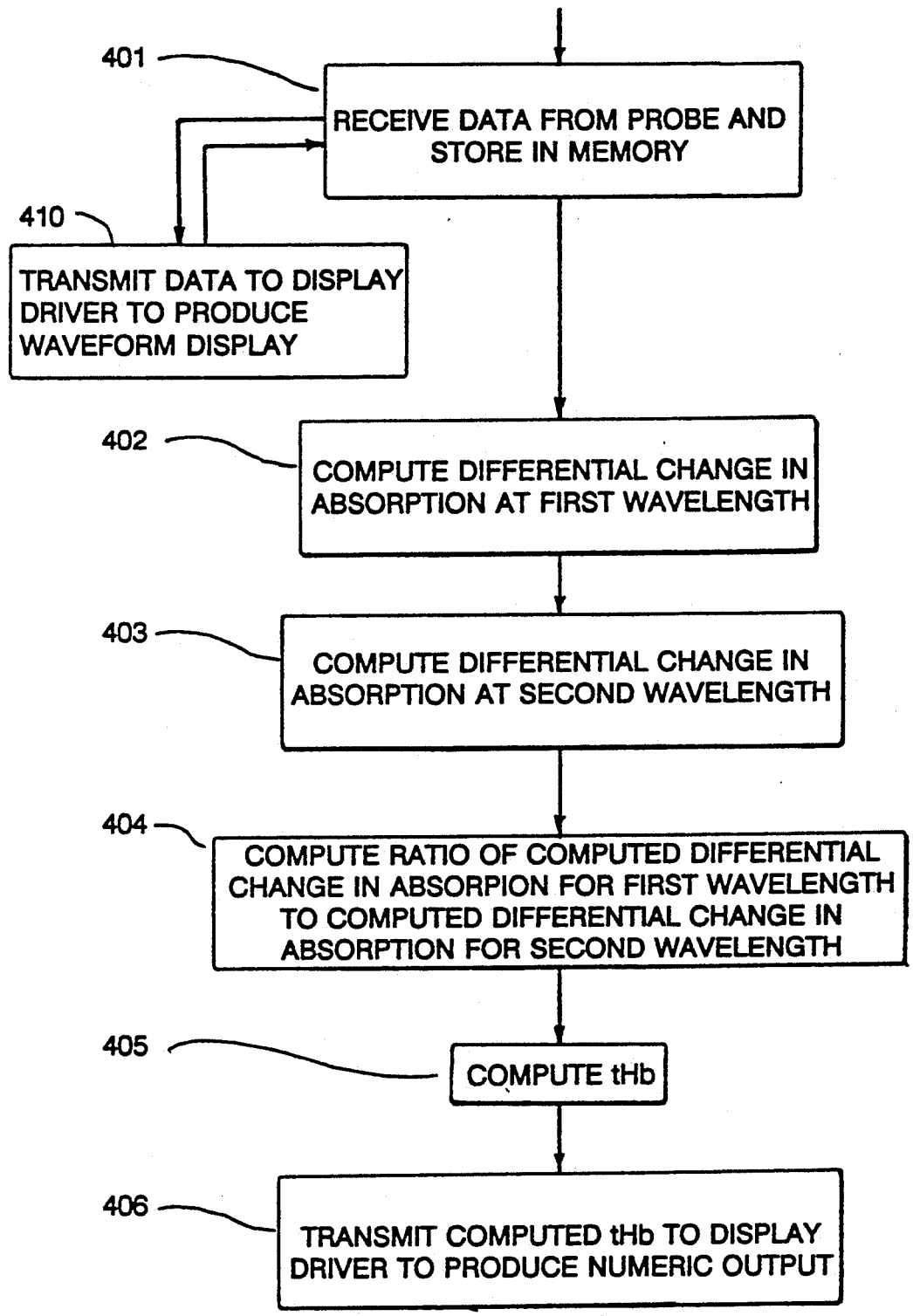
FIG. 4 illustrates in flow diagram form the operational steps taken by a two wavelength arterial blood monitoring system to measure selected components in arterial blood.

In a two wavelength system, data processing circuit 107 computes a ratio from the digital amplitude data measured at each wavelength of light. In particular, this process used by data processing circuit 107 is illustrated in flow diagram form in FIG. 4. At step 401, data processing circuit 107 receives a set of digital input data indicative of the measured intensity of light at both wavelengths, as received by light detector 113. Data processing circuit 107 at step 410 transmits the received set of data to display driver 109 for display in graphical form on display 114. The displayed waveform represents the pulsatile component of the arterial blood. Data processing circuit 107 also stores the received set of data in memory 106 and uses this set of data and the last most recently received set of data to compute at steps 402 and 403 the differential change in absorption of the arterial blood in finger 105 at the first and second selected wavelengths of light, respectively. The differential change in absorption at wavelength n is computed by data processing circuit 107 as:

$$dA_n = \frac{dI_n}{I_n} \quad (1)$$

Because $dI_n$ is a mathematical construct, it is approximated in arterial blood monitoring system 100 by $\Delta I_n$, where $\Delta I_n$ is the difference between two consecutively received $I_n$ values. Only $\Delta I$ values that are caused by a small but non zero change in path length through finger 105 are used and therefore $\Delta I_n$ can also be a longer interval of time if necessary to obtain a sufficient change in received intensity of the beam of light. The $I_n$ value used in equation 1 is the average of the two successively received $I_n$ values used to compute $\Delta I_n$.

In a two wavelength system, a final ratio is then calculated by data processing circuit 107 at step 404 as:

$$R = \frac{dA_1}{dA_2} \quad (2)$$

where the data values used to compute $dA_1$ are from the same points in time as the data values used to compute $dA_2$.

This ratio is then used in a calibration equation by data processing circuit 107 at step 405 to relate the R value to a specific blood analyte value. For example, when measuring total hemoglobin, the calibration equation is approximated by a second order polynomial of the form:

$$tHb = AR^2 + BR + C \tag{3}$$

Where A, B, and C are constants that depend on the specific wavelengths of light used.

The tHb value is then output by data processing circuit 107 at step 406 to display driver 109 (and/or hardcopy) to display in human-readable form on display 115 a numeric value of the concentration of total hemoglobin in the arterial blood of finger 105. Processing then returns to step 401.

Theory

This device is based on the theory that:

$$dA_n^s = \epsilon_n^s C^s dL^s \tag{4}$$

A differential change in absorption at a given wavelength n to a given substance ($dA_n^s$), is equal to the extinction of that substance ($\epsilon_n^s$) times the concentration ($C^s$) of that substance times the differential change in pathlength of that substance ($dL^s$).

Further the differential change in absorption can be defined as:

$$dA_n = \frac{dI_n}{I_n} \tag{5}$$

Note that no measurement of the incident light intensity, Io, is required to measure the differential change in absorption dA. However, samples of $I_n$ must be taken sufficiently close in time so that $\Delta I_n$ represents a good mathematical approximation of $dI_n$.

To determine the relative proportions of two dominant absorbers, in this case water and hemoglobin, one chooses two wavelengths of light at which the two absorbers have extinctions, such that the following set of simultaneous equations has a unique solution for all possible concentrations and pathlengths of the two absorbers.

$$dA_1 = \epsilon_1^t dL^t + \epsilon_1^w dL^w \tag{6}$$

$$dA_2 = \epsilon_2^t dL^t + \epsilon_2^w dL^w \tag{7}$$

In this system of equations it is assumed that the only components which change in pathlength are those of the arterial blood. Further it is assumed that the primary absorbers are those of water and hemoglobin where the hemoglobin species in the blood are essentially only those of oxyhemoglobin and reduced hemoglobin. Choosing a wavelength of light that represents an isobestic point for the two species of hemoglobin, such as 804 manometers, minimizes the effects of changes in oxygen saturation on the total hemoglobin readings. Notice that in equations 6 and 7 above, the concentration term expressed in equation 4 has been eliminated. By viewing the optical system as compartmentalized, that is, looking at the tissue under test as one in which the light first passes through 100% skin tissue, followed by 100% venous blood, followed by 100% arterial hemoglobin, followed by 100% water, and so on, the concentration terms expressed by equation 4 are actually constants. Thus, beginning with equation 6, the extinction coefficients are meant to represent the combination of the actual extinction coefficient and the actual concentration for 100% of any given absorber.

In the system of equations (Equations 6, 7) the extinction $\epsilon$ values are constants and it is the job of the arterial blood monitoring system 100 to read the differential change in absorption (dA values) as accurately as possible. This leaves only the values of the differential path lengths dL as unknowns. With two equations, the two dL values can be uniquely and simply solved for.

Writing the proportion of hemoglobin in the arterial blood as:

$$\text{Proportion } Hb = \frac{dL^t}{dL^t + dL^w} \tag{8}$$

While this proportion is not directly the tHb, it is directly related to it. And while this relationship could be theoretically derived, an empirical relationship (as defined in equation 3) is measured instead. This is necessary due to several ways in which the true optical system of living tissues and realistic optical elements deviate from the exact theoretical model developed here. Equation 3 is therefore referred to as the calibration equation and its coefficients A, B, and C, are experimentally derived via clinical testing. The coefficients are then installed in the arterial blood monitoring system software. It should be noted that these coefficients differ for different wavelength emitters.

The wavelengths of light produced by light emitting devices 111, 112 are also selected so as to optimize the performance of the entire electro optical system: low enough light absorption so that sufficient optical signal is received by light detector 113 and high enough light absorption so that there is an appreciable change in light absorption over the range of physiological changes in pathlength caused by the pulsation of arterial blood. Typical wavelengths of light selected for a realization of this system are 810 nm and 1270 nm, however many wavelength combinations meeting the above criteria can be used.

Probe

Probe 101 contains a minimum of two lights emitting devices 111, 112, each of which produces a beam of light centered about a selected wavelength (810 nm and 1270 nm, respectively). Probe 101 also contains light detector 113 capable of receiving the emitted wavelengths of light. In the present implementation, the light detector 113 consists of a multiple layer element, shown in additional detail in FIG. 3, that contains a germanium photodiode 113b placed under a silicon photodiode 113a. For the wavelengths of light shorter than approximately 1000 nm, the silicon photodiode 113a receives the incident light. Above this wavelength, the silicon photodiode 113a becomes transparent and the germanium photodiode 113b picks up the incident light. Probe 101 includes a cable 103 and connector 103a for transmitting and receiving signals between probe 101 and probe interface circuit 102. Probe 101 is positioned on the tissue either in the transmission mode: light emitting devices 111, 112 on one side and light detector 113 on the other side of finger 105, earlobe, toe or other appropriate site through which light can be received by the light detector 113 at acceptable signal levels; or in the reflectance mode: in which the light emitting device 111, 112 and light detector 113 are placed on the same side of the tissue under test, such as the forehead or forearm.

Combination tHb Monitor and Pulse Oximeter

The methodologies for pulse oximetry are well known. The method of obtaining tHb noninvasively and in real time has been disclosed above. The arterial blood monitoring system of the present invention can combine the two technologies to create a device for measurement of both parameters. tHb is an interfering substance in the measurement of $S_aO_2$ by the present technologies. By "interfering substance" it is meant that variations in tHb cause variations in the $S_aO_2$ as ready by a pulse oximeter. These variations in $S_aO_2$ are correlated to, but not corrected for, the tHb level. A device capable of measuring tHb can therefor provide a means for eliminating the error it causes in determining $S_aO_2$. The same holds true in terms of $S_aO_2$ being an interfering substance in the measurement of tHb. An iteration to this problem lies in a combination device capable of reading both parameters. Such a device can be simply obtained by using two wavelengths to derive the $S_aO_2$, and two more as described above for obtaining tHb. The resulting values for $S_aO_2$ and Thb can then be used to correct the readings of the other. A more sophisticated system uses a three wavelength system, where the practical realization of this system utilizes the standard oximetry wavelengths of 660 nm and 940 nm produced by two light emitting devices 111a, 111b, along with a wavelength of 1270 nm produced by a light emitting device 112. (Once again, any three wavelengths that meet the criteria stated above for a standalone tHb system can be used.) In addition, the two segment light detector 113 is activated in a manner to reflect the use of three wavelengths of light. Silicon photodiode 113a detects both of the light beams (660 nm, 940 nm) produced by light emitter devices 111a, 111b and its output is demultiplexed to separate the two measured values of light intensity. Germanium photodiode 113b of light detector 113 measures the intensity of the third beam light at 1270 nm.

Figure 5:
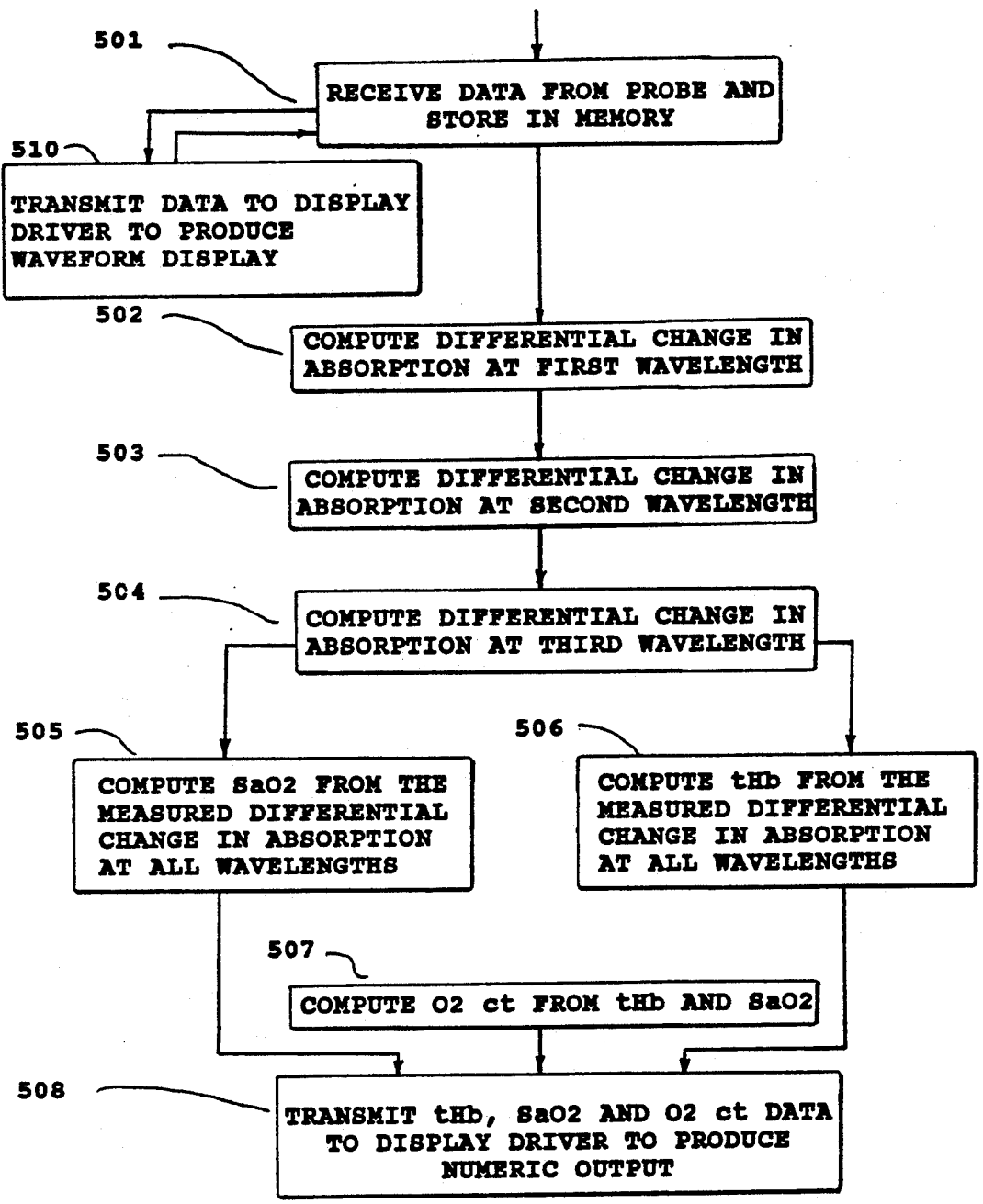
FIG. 5 illustrates in flow diagram form the operational steps taken by a three wavelength arterial blood monitoring system to measure selected components in arterial blood.

In particular, the process used by data processing circuit 107 is illustrated in flow diagram form in FIG. 5. At step 501, data processing circuit 107 receives a set of digital input data indicative of the measured intensity of light at all three wavelengths, as received by light detector 113. Data processing circuit 107 at step 510 transmits the received set of data to display driver 109 for display in graphical form on display 114. The displayed waveform represents the pulsatile component of the arterial blood. Data processing circuit 107 also stores the received set of data in memory 101 and uses this set of data and the last most recently received set of data to compute at steps 502–504 the differential change in absorption of the arterial blood in finger 105 at the first, second, and third wavelengths of light, respectively.

Thus, as noted above, and extrapolated to a three variable system:

$$dA_\lambda = \epsilon_\lambda^O dL^O + \epsilon_\lambda^R + \epsilon_\lambda^W \quad (9)$$

where
$O = [O_2Hb]$ $R = [RHb]$ $W = [H_2O]$

Therefore at any given wavelength, $\lambda$, the differential change in light absorption is a function of the change in path length of the three absorbers: oxyhemoglobin ($O_2Hb$), reduced hemoglobin (RHb), and water ($H_2O$).

$$tHb \propto \frac{dL^O + dL^R}{dL^O + dL^R + + dL^W} \quad (10)$$

Note that this equation shows only that the total hemoglobin is proportional to this ratio of path length changes, not equal to it. This is due, at least in part, to the fact the tHb is measured in terms of grams/deciliter of whole blood and this equation is a ratio of path lengths. There is a one to one correspondence between this ratio of path lengths and the tHb which is determined, and curve fit, experimentally. The empirical curve fit also compensates for the differences between the theoretical models and the actual optical systems.

$$S_aO_2 = \frac{dL^O}{dL^O + dL^R} \quad (11)$$

For a three wavelength system, with the subscripts 1, 2, and 3 indicating the specific wavelengths used we can write following system of equations $$dA_1 = \epsilon_1^O dL^O + \epsilon_1^R dL^R + \epsilon_1^W dL^W \quad (12)$$

$$dA_2 = \epsilon_2^O dL_O + \epsilon_2^R dL^R + \epsilon_2^W dL^W \quad (13)$$

$$dA_3 = \epsilon_3^O dL^O + \epsilon_3^R dL^R + \epsilon_3^W dL^W \quad (14)$$

In matrix notation:

$$\begin{pmatrix} dA_1 \\ dA_2 \\ dA_3 \end{pmatrix} = \begin{pmatrix} dL^O \\ dL^R \\ dL^W \end{pmatrix} \begin{pmatrix} \epsilon_1^O & \epsilon_1^R & \epsilon_1^W \\ \epsilon_2^O & \epsilon_2^R & \epsilon_2^W \\ \epsilon_3^O & \epsilon_3^R & \epsilon_3^W \end{pmatrix} \quad (15)$$

This allows us to solve for the path length contributions of each of the three absorbers as defined by the following equations $$dL^O = \frac{dA_1(\epsilon_2^R \epsilon_3^W - \epsilon_3^R \epsilon_{2W}) - dA_2(\epsilon_1^R \epsilon_3^W - \epsilon_3^R \epsilon_1^W) + dA_3(\epsilon_1^R \epsilon_2^W - \epsilon_2^R \epsilon_1^W)}{\Delta} \quad (16)$$

$$dL^R = \frac{\epsilon_1^O(dA_2 \epsilon_3^W - dA_3 \epsilon_2^W) - \epsilon_2^O(dA_1 \epsilon_3^W - dA_3 \epsilon_1^W) + \epsilon_3^O(dA_1 \epsilon_2^W - dA_2 \epsilon_1^W)}{\Delta} \quad (17)$$

$$dL^W = \frac{\epsilon_1^O(\epsilon_2^R dA_3 - \epsilon_3^R dA_2) - \epsilon_2^O(\epsilon_1^R dA_3 - \epsilon_3^R dA_1) + \epsilon_3^O(\epsilon_1^R dA_2 - \epsilon_2^R dA_1)}{\Delta} \quad (18)$$

Now the $S_aO_2$ can be calculated by data processing circuit 107 at step 405 as $$S_aO_2 = \frac{dL^O}{dL^O + dL^R} \quad (19)$$

-continued $$[dA_1(\epsilon_2^R\epsilon_3^W - \epsilon_3^R\epsilon_2^W) - dA_2(\epsilon_1^R\epsilon_3^W - \epsilon_3^R\epsilon_1^W) + \quad (20)$$
$$= \frac{dA_3(\epsilon_1^R\epsilon_2^W - \epsilon_2^R\epsilon_1^W)]/\Delta}{[dA_1(\epsilon_2^R\epsilon_3^W - \epsilon_3^R\epsilon_2^W) - dA_2(\epsilon_1^R\epsilon_3^W - \epsilon_3^R\epsilon_1^W) +}$$
$$dA_3(\epsilon_1^R\epsilon_2^W - \epsilon_2^R\epsilon_1^W) + \epsilon_1^O(dA_2\epsilon_3^W - dA_3\epsilon_2^W) -$$
$$\epsilon_2^O(dA_1\epsilon_3^W - dA_3\epsilon_1^W) + \epsilon_3^O(dA_1\epsilon_2^W - dA_2\epsilon_1^W)]/\Delta$$

$$dA_1(\epsilon_2^R\epsilon_3^W - \epsilon_2^W\epsilon_3^R) - dA_2(\epsilon_1^R\epsilon_3^W - \epsilon_1^W\epsilon_3^R) + \quad (21)$$
$$= \frac{dA_3(\epsilon_1^R\epsilon_2^W - \epsilon_1^W\epsilon_2^R)}{dA_1(\epsilon_2^R\epsilon_3^W - \epsilon_2^W\epsilon_3^R - \epsilon_2^O\epsilon_3^W + \epsilon_2^W\epsilon_3^O) +}$$
$$dA_2(\epsilon_1^W\epsilon_3^R - \epsilon_1^R\epsilon_3^W + \epsilon_1^O\epsilon_3^W - \epsilon_1^W\epsilon_3^O) +$$
$$dA_3(\epsilon_1^R\epsilon_2^W - \epsilon_2^R\epsilon_1^W - \epsilon_1^O\epsilon_2^W + \epsilon_2^O\epsilon_1^W)$$

Recognizing that the extinction coefficients are empirically measured constants, using $K_1$ through $K_6$ to indicate the appropriate combination of extinction coefficients, we can simplify the equation for $S_aO_2$ as follows $$S_aO_2 = \frac{dA_1(K_1) + dA_2(K_2) + dA_3(K_3)}{dA_1(K_4) + dA_2(K_5) + dA_3(K_6)} \quad (22)$$

The same development that was performed for $S_aO_2$ can now be done by data processing circuit 107 at step 406 for total hemoglobin. Notice that the numerator in this equation is identical to the denominator in the equation for $S_aO_2$.

$$tHb \propto \frac{dL^O + dL^R}{dL^W + dL^O + dL^R} \quad (23)$$

$$dA_1(\epsilon_2^R\epsilon_3^W - \epsilon_2^W\epsilon_3^R - \epsilon_2^O\epsilon_3^W + \epsilon_2^W\epsilon_3^O) + \quad (24)$$
$$dA_2(\epsilon_1^W\epsilon_3^R - \epsilon_1^R\epsilon_3^W + \epsilon_1^O\epsilon_3^W - \epsilon_3^O)$$
$$tHb \propto \frac{dA_3(\epsilon_1^R\epsilon_2^W - \epsilon_2^R\epsilon_1^W + \epsilon_2^O\epsilon_1^W - \epsilon_1^O\epsilon_2^W)}{dA_1(\epsilon_2^O\epsilon_3^R - \epsilon_2^R\epsilon_3^O + \epsilon_2^W\epsilon_3^O - \epsilon_2^O\epsilon_3^W +}$$
$$\epsilon_2^R\epsilon_3^W - \epsilon_3^R\epsilon_2^W) + dA_2(\epsilon_1^R\epsilon_3^O - \epsilon_1^O\epsilon_3^R +$$
$$\epsilon_1^O\epsilon_3^W - \epsilon_1^W\epsilon_3^O + \epsilon_1^W\epsilon_3^R - \epsilon_1^R\epsilon_3^W) +$$
$$dA_3(\epsilon_1^O\epsilon_2^R - \epsilon_1^R\epsilon_2^O + \epsilon_2^O\epsilon_1^W -$$
$$\epsilon_2^W\epsilon_1^O + \epsilon_1^R\epsilon_2^W - \epsilon_1^W\epsilon_2^R)$$

$$tHb \propto \frac{dA_1(K_4) + dA_2(K_5) + dA_3(K_6)}{dA_1(K_7) + dA_2(K_8) + dA_3(K_9)} \quad (25)$$

Oxygen Content

With tHb and $S_aO_2$ known it is a simple matter to calculate and display the O2 content of the arterial blood. This is derived by data processing circuit 107 at step 407 as follows:

$$O_2ct = (0.0031 * PO_2) + (1.38 * tHb * S_aO_2) \quad (26)$$

tHb and $S_aO_2$ are the analytes measured by the arterial blood monitoring system and Po2 can either be taken as a fixed value of 90 torr or for increased accuracy can be obtained by working backwards through the oxygen dissociation curve. The curve can be installed as a look-up table in memory 107 or an equation in the software of data processing circuit 107. As the pH, 2,3 DPG and PaCO2 are unknown, the curve used assumes an average or normal level for these variables. Since the dissolved oxygen is such a small contribution to the total O2 ct, either of these methods provides adequate accuracy. At step 508, data processing circuit 107 transmits the computed values of $S_aO_2$, tHb and O2 ct to display driver 109 to produce numerical human-readable outputs on display devices 115a, 115b, 115c, respectively.

There are several different methodologies that accomplish the same purpose. One of these is a logarithmically based method. In this method, equation 1 is modified as follows:

$$R_n = \frac{\log I_{n(systole)}}{\log I_{n(diastole)}} \quad (27)$$

and equation 2 becomes:

$$R = \frac{R_1}{R_2} \quad (28)$$

The log values are to the base e. Systole and diastole refer to the two points on the photoplethysmographic waveform where the transmitted intensity is sampled.

These log values can be calculated (or obtained via lookup table in memory 106) by data processing circuit 107 using the circuitry already defined. Alternatively the circuitry can be altered to utilize logarithmic amplifiers so that the data sampled by data processing circuit 107 is already converted to logarithms or is the final ratio calculated in equation 2. One advantage of this methodology is that it allows one to work with the max and min values of the photoplethysmographic waveform. It is worth noting that the sample points on the photoplethysmographic waveform do not necessarily have to be at systole and diastole. They can be any two points separated by a measurable change in arterial path length.

Light Detector Architecture

Figure 3:
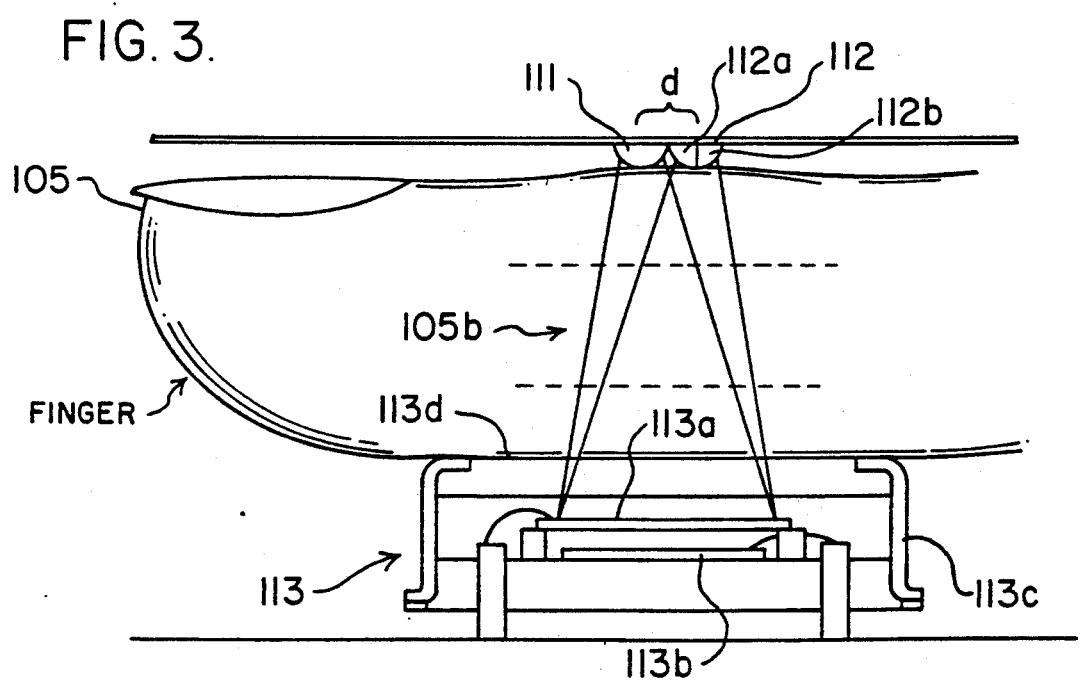
FIG. 3 illustrates a cross-section view of the light detector used in the probe of the present invention.

The basic architecture of light detector 113 is illustrated in additional detail in FIG. 3. The light detector device 113 is comprised of a pair of photodetectors 113a, 113b, mounted in a "sandwich" configuration. Light detector 113 can be a device such as the J16Si-8 Germanium/Silicon Detector manufactured by E, G & G Photon Devices, of Salem, Mass. The light detector 113 illustrated in FIG. 3 comprises a high performance silicon photodiode 113a mounted over a germanium photodiode 113b, hermetically sealed in a package 113c, which package 113c includes a transparent window 113d to admit the beams of light transmitted through appendage 105. The silicon photodiode 113a responds to light that is of wavelength 400 to 1000 nanometers, while the germanium photodiode 113b responds to light that is of wavelength 1000 to 1800 nanometers. The longer wavelength light beam passes through the silicon photodiode 113a and shines on the germanium photodiode 113b mounted below. As can be seen from FIG. 3, the two beams of light produced by light sources 111, 112, of wavelength 810 nanometers and 1270 nanometers, respectively, pass along a light path that is substantially common as the two light beams traverse appendage 105 to reach the single light detector 113. The arteriolar bed 105b contained in appendage 105 is not located along the surface of appendage 105 and thus the two light beams are coextensive as they traverse the arteriolar bed 105b. Since it is the change in the path length of the light beams as they pass through the arteriolar bed 105b that is critical to the accuracy of the measurements being taken, the creation of a common light path through the arteriolar bed 105b significantly improves the accuracy of the measurements taken. If two light beams were incident on two separate light detectors, separated from each other by a distance d, this introduces error into the measurements, since two measurements are taken of the change in path length of two different light paths through two different sections of the arteriolar bed 105b, separated by a distance d. Typical dimensions of a light detector are 1 to 5 mm in diameter. There is a need for two light detectors 113a, 113b since the two wavelengths of light selected (810 nm, 1270 nm) cannot be detected adequately by a single light detector device. The lateral juxtaposed positioning of the two light detector devices 113a, 113b would introduce errors, as noted above, and the vertical juxtaposed positioning in a "sandwich" configuration minimizes the errors introduced by different light paths through arteriolar bed 105b, by transmitting the two beams of light over substantially the same light path through arteriolar bed 105b in appendage 105. For the same reason, the distance d between light sources 111 and 112 should also be minimized. A typical light source includes 15 mil LEDs located on 50 mil centers. For the three wavelength system disclosed above, light source 112 can be implemented by a pair of light emitting devices 112a, 112b.

While a specific embodiment of this invention has been disclosed, it is expected that those skilled in the art can and will design alternate embodiments of this invention that fall within the scope of the appended claims.

I claim:

1. A probe for noninvasively measuring components contained in arterial blood in a subject, which components include a plurality of dominant absorbers, by producing data indicative of a change in light absorption as a function of a change in path length in said arterial blood in said subject at a plurality of predetermined wavelengths of light, comprising:
    a plurality of light source means for transmitting a plurality of beams of light, at a plurality of predetermined wavelengths of light along a substantially identical light path through said arterial blood; and
    means for measuring a change in light absorption of said plurality of beams of light transmitted through said arterial blood, indicative of said change in path length at said plurality of wavelengths of light through said arterial blood along said substantially identical light path, comprising:
        first light detector means for measuring the magnitude of a first of said plurality of beams of light transmitted at a first of said plurality of wavelengths of light along said substantially identical light path:
        second light detector means for measuring the magnitude of a second of said plurality of beams of light transmitted at a second of said plurality of wavelengths of light along said substantially identical light path; and
        wherein said first and said second light detector means are mounted coaxially along said substantially identical light path.

2. The probe of claim 1 wherein said first light detector means is mounted on top of said second light detector means in a sandwich configuration, wherein said first and second light detector means are coaxial with said substantially identical light path.

3. The probe of claim 2 wherein said second beam of light is transmitted through said first light detector means to said second light detector means.

4. The probe of claim 1 wherein said first light detector means is interposed between said second light detector means and said arterial blood along said substantially identical light path.

5. A probe for noninvasively measuring components contained in arterial blood in a subject, which components includes a plurality of dominant absorbers, by producing data indicative of a change in light absorption as a function of a change in path length in said arterial blood in said subject at a plurality of predetermined wavelengths of light, comprising:
    a plurality of light source means for transmitting a plurality of beams of light, at a plurality of predetermined wavelengths of light along a substantially identical light path through said arterial blood; and
    means for measuring a change in light absorption of said plurality of beams of light transmitted through said arterial blood, indicative of said change in path length at said plurality of wavelengths of light through said arterial blood along said substantially identical light path;
    wherein a first and a second of said plurality of dominant absorbers are water and hemoglobin, which contains oxygenated and deoxygenated components, wherein a first light source means produces a first beam of light at a wavelength of approximately 810 nanometers and a second light source means produces a second beam of light at a wavelength of approximately 1270 nanometers, said measuring means comprises:
        first light detector means comprising a silicon photodiode light detector responsive to wavelengths of light in and around 810 nanometers;
        second light detector means, comprising a germanium photodiode light detector responsive to wavelengths of light in and around 1270 nanometers; and
        wherein said first and said second light detector means are mounted coaxially along said substantially identical light path.

6. The probe of claim 5 wherein said first light detector means is mounted on top of said second light detector means in a sandwich configuration, wherein said first and second light detector means are coaxial with said substantially identical light path.

7. The probe of claim 6 wherein said second beam of light is transmitted through said first light detector means to said second light detector means.

8. A probe for noninvasively measuring components contained in arterial blood in a subject, which components include a plurality of dominant absorbers, by producing data indicative of a change in light absorption as a function of a change in path length in said arterial blood in said subject at a plurality of predetermined wavelengths of light, comprising;
    a plurality of light source means for transmitting a plurality of beams of light, at a plurality of predetermined wavelengths of light along a substantially identical light path through said arterial blood;
    means for measuring a change in light absorption of said plurality of beams of light transmitted through said arterial blood, indicative of said change in path length at said plurality of wavelengths of light through said arterial blood along said substantially identical light path;
    wherein said first and second dominant absorbers are water and hemoglobin, which contains oxygenated and deoxygenated components, wherein a first light source means produces a first beam of light at a wavelength of approximately 660 nanometers and a second light source means produces a second beam of light at a wavelength of approximately 940 nanometers and a third light source means produces a third beam of light at a wavelength of approximately 1270 nanometers, said measuring means comprises:

first light detector means comprising a silicon photodiode light detector responsive to wavelengths of light in and around 660 and 940 nanometers;

second light detector means, comprising a germanium photodiode light detector responsive to wavelengths of light in and around 1270 nanometers; and wherein said first and second light detector means are mounted coaxially along said substantially identical light path.

9. The probe of claim 8 wherein said first light detector means is mounted on top of said second light detector means in a sandwich configuration, wherein said first and second light detector means are coaxial with said substantially identical light path.

10. The probe of claim 9 wherein said third beam of light is transmitted through said first light detector means to said second light detector means.